United States Patent
Plahey

(10) Patent No.: US 11,273,246 B2
(45) Date of Patent: Mar. 15, 2022

(54) PISTON ASSEMBLY INCLUDING LEAK DETECTION IN A DIALYSIS MACHINE

(71) Applicant: Fresenius Medical Care Holdings, Inc., Waltham, MA (US)

(72) Inventor: Kulwinder S. Plahey, Martinez, CA (US)

(73) Assignee: Fresenius Mesical Care Holdings, Inc., Waltham, MA (US)

(*) Notice: Subject to any disclaimer, the term of this patent is extended or adjusted under 35 U.S.C. 154(b) by 260 days.

(21) Appl. No.: 16/680,778

(22) Filed: Nov. 12, 2019

(65) Prior Publication Data
US 2021/0138140 A1    May 13, 2021

(51) Int. Cl.
| | |
|---|---|
| A61M 1/28 | (2006.01) |
| G01M 3/04 | (2006.01) |
| G01M 3/16 | (2006.01) |
| G08B 7/00 | (2006.01) |

(52) U.S. Cl.
CPC ......... *A61M 1/282* (2014.02); *A61M 2205/12* (2013.01); *A61M 2205/15* (2013.01); *A61M 2205/3317* (2013.01); *A61M 2205/502* (2013.01); *A61M 2205/581* (2013.01); *A61M 2205/587* (2013.01); *G01M 3/04* (2013.01); *G01M 3/045* (2013.01); *G01M 3/16* (2013.01); *G08B 7/00* (2013.01)

(58) Field of Classification Search
None
See application file for complete search history.

(56) References Cited

U.S. PATENT DOCUMENTS

| | | |
|---|---|---|
| 5,674,390 A | 10/1997 | Matthews et al. |
| 7,973,667 B2 | 7/2011 | Crnkovich et al. |
| 8,950,241 B2 | 2/2015 | Hedmann et al. |
| 8,973,424 B2 | 3/2015 | Wiktor |

(Continued)

FOREIGN PATENT DOCUMENTS

| | | |
|---|---|---|
| DE | 102014010906 A1 | 1/2016 |
| WO | 2018115816 A1 | 6/2018 |

OTHER PUBLICATIONS

International Search Report and Written Opinion for International application No. PCT/US2020/054479, dated Jan. 19, 2021, 19 pages.

*Primary Examiner* — Paul M. West
*Assistant Examiner* — Mark A Shabman
(74) *Attorney, Agent, or Firm* — Kacvinsky Daisak Bluni PLLC

(57) ABSTRACT

Dialysis systems and methods for operating dialysis machines (e.g., peritoneal dialysis machines) for conducting dialysis treatments are disclosed. The dialysis system may include a dialysis machine for transferring dialysate to a patient from a dialysate source. The dialysate may flow from the dialysate source through a cartridge or cassette (e.g., a disposable cartridge or cassette) positionable within the dialysis machine. The dialysis machine includes a piston for pumping fluid (e.g., dialysate) from the cassette to the patient. In various embodiments, during use, the piston is arranged and configured to contact, compress, etc. a membrane defining one or more fluid chambers in the cassette. In one embodiment, the piston includes a sensor for detecting a leak at the interface between the piston and the membrane. The sensor may be a capacitive sensor.

9 Claims, 7 Drawing Sheets

(56) References Cited

U.S. PATENT DOCUMENTS

| | | |
|---|---|---|
| 9,555,178 B2 | 1/2017 | Kotsos et al. |
| 9,561,323 B2 | 2/2017 | Plahey et al. |
| 2003/0217962 A1 | 11/2003 | Childers et al. |
| 2009/0008306 A1 | 1/2009 | Cicchello et al. |
| 2009/0322543 A1 | 12/2009 | Crnkovich et al. |
| 2010/0140149 A1 | 6/2010 | Fulkerson et al. |
| 2014/0251583 A1 | 9/2014 | Eriksen |
| 2016/0166757 A1* | 6/2016 | Koyama ............... G01N 27/08 324/693 |
| 2018/0207588 A1 | 7/2018 | Crnkovich et al. |
| 2019/0015577 A1 | 1/2019 | Garrido et al. |
| 2019/0262522 A1 | 8/2019 | Wyeth et al. |
| 2019/0358381 A1* | 11/2019 | Westenbrink ........... F04B 51/00 |

\* cited by examiner

PISTON ASSEMBLY INCLUDING LEAK DETECTION IN A DIALYSIS MACHINE

FIELD OF THE DISCLOSURE

The disclosure generally relates to dialysis machines, and more particularly to a piston assembly in a dialysis machine, the piston assembly including a leak detector.

BACKGROUND

Dialysis machines are known for use in the treatment of renal disease. The two principal dialysis methods are hemodialysis (HD) and peritoneal dialysis (PD). During HD, the patient's blood is passed through a dialyzer of an HD machine while also passing dialysate through the dialyzer. A semi-permeable membrane in the dialyzer separates the blood from the dialysate within the dialyzer and allows diffusion and osmosis exchanges to take place between the dialysate and the blood stream. During PD, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated PD machines, called PD cyclers, are designed to control the entire PD process so that it can be performed at home, usually overnight, without clinical staff in attendance.

A dialysis machine, such as a PD machine, may include one or more containers (e.g., bags) containing a fluid (e.g., a dialysate) for patient infusion. In addition, a PD machine may include a removable and/or replaceable cartridge or cassette (used interchangeably without the intent to limit) attached to one or more fluid lines for pumping fluid to and from a patient. In PD machines, for example, one or more fluid lines are inserted into an abdomen of a patient for flowing fresh dialysate and removing used dialysate, waste, and excess fluid. As the cassette facilitates pumping of the fluid, the dialysis machine may monitor fluid delivery, fluid temperature, flow path, and pressure.

The cassette may be insertable into the PD machine and enclosed within the PD machine during a dialysis operation. At the conclusion of the operation, the cassette may be removed and properly disposed of. The cassette and accompanying fluid flow lines, valves, and/or connectors may be single use items.

In use, the PD machines and cassette include an interface where a pump mechanism of the PD machine contacts the cassette. That is, the cassette typically includes a membrane such as, for example, a rigid material that forms one or more channels, pump chambers, etc. in the cassette. The rigid material may be bonded to a flexible membrane that can be distorted by the pump mechanism of the PD machine. The fluid (e.g., dialysate) may be contained between the rigid material and the flexible membrane. In use, the fluid (e.g., dialysate) may be moved from the PD machine to the patient via the action of a piston or pump head in the PD machine on the membrane of the cassette.

In some cases, the cassette may include manufacturing defects where, for example, the flexible membrane may not be fully bonded to the rigid material or where the flexible membrane and/or rigid material includes a hole or tear. Alternatively, the cassette may become damaged during shipping, storing, insertion, etc. Whatever the situation, in some cases, the cassette may become damaged causing fluid (e.g., dialysate) to leak from the cassette. Cassette leaking may affect the quality of the fluid flow and the exchange of the dialysate with the patient, potentially affecting a patient's treatment procedure (e.g., dialysate may not be delivered to the patient's peritoneal cavity or incorrect amounts of fluid may be delivered or removed from the patient's peritoneal cavity). In addition, when leaks develop and remain undetected in the PD machine, leaking fluid may damage the PD machine, possibly beyond repair, requiring full replacement. This can be problematic when a patient requires frequent dialysis treatment and needs to obtain an immediate replacement, which can be costly.

A leak developed at the interface between the piston or pump head of the pump mechanism in the PD machine and the membrane proximate the pump chamber of the cassette can be particularly problematic since the pump chamber contains one of the largest volume of fluid collection in the cassette and, therefore, a leak at this location can lead to large amounts of leaking fluid. As such, it would be advantageous to detect a leak right at, or adjacent to, the interface between the piston or pump head and the membrane of the cassette.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a dialysis system for conducting a dialysis treatment is disclosed. The dialysis system comprises a dialysis machine for transferring dialysate to a patient from a dialysate source, the dialysis machine including a housing including a cavity, a pump positioned within the housing, and a sensor associated with the pump. The dialysis system further comprises a cassette positionable within the cavity, the cassette being in fluid communication with the patient and the dialysate source; wherein, when the cassette is positioned within the cavity, movement of the pump causes dialysate to be transferred from the dialysate source to the patient, the sensor being arranged and configured to detect a presence of fluid.

In this and other embodiments, the sensor is a capacitive sensor arranged and configured to detect the presence of fluid.

In this and other embodiments, the capacitive sensor is positioned within the pump.

In this and other embodiments, the capacitive sensor is positioned on a front surface of the pump.

In this and other embodiments, the capacitive sensor is arranged and configured to detect the presence of fluid on one of an outer surface of the cassette and on the front surface of the pump.

In this and other embodiments, the sensor is configured to send a signal based on a detection of fluid with the sensor to indicate a leak condition; wherein the signal is sent to a user interface of the dialysis machine, an audible indicator, or a light indicator, or a combination thereof.

In this and other embodiments, the dialysis machine is arranged and configured to automatically terminate the transfer of dialysate to the patient from the dialysate source upon receipt of the signal.

According to an exemplary embodiment of the present disclosure, a method for detecting a leak in a dialysis machine is disclosed. The method comprises operating the dialysis machine to transfer dialysate to a patient from a dialysate source, the dialysis machine including a housing including a cavity, and a pump positioned within the housing for facilitating transfer of the dialysate; and monitoring a leak condition by a leak detector, the leak detector being a capacitive sensor operatively associated with the pump, wherein a leak is detectable in response to fluid contacting the capacitive sensor.

In this and other embodiments, the capacitive sensor is disposed within a front surface of the pump; or on a front surface of the pump; or a combination thereof.

In this and other embodiments, the method further comprises positioning a cassette within the cavity, the cassette being in fluid communication with the patient and the dialysate source.

In this and other embodiments, during operation of the dialysis machine, the pump contacts the cassette, the capacitive sensor being arranged and configured to detect a presence of fluid.

In this and other embodiments, the capacitive sensor is arranged and configured to detect the presence of fluid on one of an outer surface of the cassette and on the front surface of the pump.

In this and other embodiments, the method further comprises, in response to fluid contact with the leak detector, sending a signal to a user interface of the dialysis machine, an audible indicator, or a light indicator, or a combination thereof, to indicate a leak condition.

In this and other embodiments, the method further comprises automatically terminating the transfer of dialysate to the patient from the dialysate source upon receipt of the signal.

According to an exemplary embodiment of the present disclosure, a dialysis system for conducting a dialysis treatment is disclosed. The dialysis system comprises a dialysis machine arranged and configured to transfer dialysate to a patient from a dialysate source, the dialysis machine including a housing including a cavity, and a pump positioned within the housing for facilitating transfer of the dialysate; and a capacitive sensor operatively associated with the pump, wherein a leak is detectable in response to fluid contacting the capacitive sensor.

In this and other embodiments, the capacitive sensor is disposed within a front surface of the pump, or on a front surface of the pump, or a combination thereof.

In this and other embodiments, the dialysis system further comprises a cassette positionable within the cavity, the cassette being in fluid communication with the patient and the dialysate source.

In this and other embodiments, during operation of the dialysis machine, the pump contacts the cassette, the capacitive sensor being arranged and configured to detect a presence of fluid.

In this and other embodiments, the capacitive sensor is arranged and configured to detect the presence of fluid on one of an outer surface of the cassette and on the front surface of the pump.

In this and other embodiments, in response to the leak, the dialysis machine is arranged and configured to transmit a signal to indicate a leak condition, the signal is sent to a user interface of the dialysis machine, an audible indicator, or a light indicator, or a combination thereof.

BRIEF DESCRIPTION OF THE DRAWINGS

By way of example, specific embodiments of the disclosed methods and devices will now be described, with reference to the accompanying drawings, in which.

DETAILED DESCRIPTION

Figure 1:
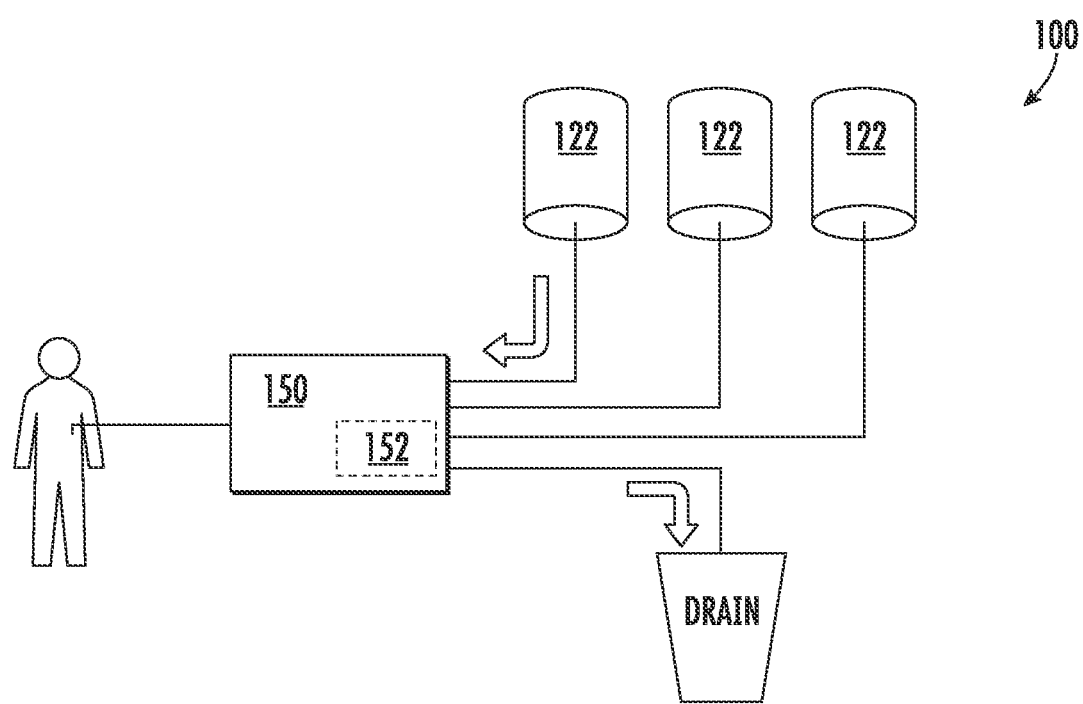
FIG. 1 illustrates an example of an embodiment of a dialysis system.

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of systems and methods arranged and configured to provide improved leak detection in a dialysis machine will now be described herein. Dialysis operation is often not able to be monitored manually on a continual basis for leaks or other fluid conditions, or it may not be efficient or practical to do so. This is particularly the case where dialysis is performed while a patient is sleeping, e.g., in the case of PD machines that are often self-administered in the home of a patient. Automatic detection and shutdown is therefore important to prevent any potential machine malfunction or delivery of improper treatment.

In accordance with one or more aspects of the present disclosure, a dialysis machine such as, for example, a PD machine, may be able to quickly detect any leaks that may develop, for example, in a cassette (e.g., disposable cassette) positioned within the PD machine, so that operation of the dialysis machine may be shut down, thereby ensuring patient safety and limiting or eliminating the potential for damage or further damage to components of the machine that are sensitive to fluid contact, e.g., electrical and electronic components. In one example of an embodiment, a piston or pump head positioned in a dialysis machine includes a sensor such as, for example, a capacitive sensor, disposed on a front surface of the piston or pump head. The sensor can detect fluid on the surface of the piston or pump head. In another example of an embodiment, a sensor can be positioned on, or adjacent to, an inlet tube of the cassette. In some embodiments, more than one sensor may be utilized with a machine. The sensors may be positioned in the same or different locations with respect to the pump and/or pump cassette.

Referring to FIG. 1, a dialysis system 100 may include a PD machine 150, for flowing fresh dialysate into a patient and draining used dialysate out of the patient. During treatment, a volume of dialysate may enter the patient's abdomen and remain for a period of time, e.g., a dwell time. During the dwell time, the dialysate may flow across the peritoneum and absorb contaminants and/or particulates from a patient's blood and exchange substances and fluids (e.g., electrolytes, urea, glucose, albumin, osmotically active particles, and other small molecules). At the end of the dwell time, the used dialysate may be flowed out of the patient's abdomen and purged to a drain connected to the tubing, e.g., the drain line. This exchange of fresh dialysate and used dialysate after a dwell time may occur for several cycles depending on the patient's treatment regimen.

One or more dialysate sources may be connected to the dialysis machine 150. In some embodiments, as illustrated, the dialysate source(s) may be dialysate bags 122 that are hung near the PD machine 150 which may improve air content management as any air content is disposed by gravity to a top portion of the dialysate bag 122. Valves may be attached to a bottom portion of the dialysate bags 122 so fluid is drawn out and air content delivery is minimized. In one embodiment, as shown, dialysate from the dialysate bags 122 may be transferred directly to the patient through a warmer pouch, a heating chamber, or the like 152 (used interchangeably without the intent to limit) formed in the dialysis machine 150. When the dialysate has reached a predetermined temperature (e.g., approximately 98°–100° F., 37° C.) in the heating chamber 152, the dialysate may be flowed into the patient. As will be described and illustrated in greater detail below, the dialysate bags 122 may be connected to a cartridge or cassette (used interchangeably without the intent to limit), which may be insertable into the dialysis machine 150. In use, the cassette may be connected to dialysate bag lines, which may be used to pass dialysate from dialysate bags 122 to the cassette. In use, the cassette may be disposable. Alternatively, the cassette may be reusable. In addition, a patient line and a drain line may be connected to the cassette. The patient line may be connected to a patient's abdomen via a catheter and may be used to pass dialysate back and forth between the cassette and the patient's peritoneal cavity during use. The drain line may be connected to a drain or drain receptacle and may be used to pass dialysate from the cassette to the drain or drain receptacle during use. Although the system described herein is discussed principally in connection with the use of dialysate bags as the dialysate source, it is noted that, in other embodiments, different dialysate sources may be used. For example, in other embodiments, the dialysate source may include one or more containers in which dialysate is mixed and/or otherwise prepared at the PD cycler from a dialysate concentrate, see, e.g., U.S. Pat. No. 10,076,599 to Eyrard et al., entitled "Dry Peritoneal Dialysis Concentrate System," which is incorporated by reference herein in its entirety.

Figure 2:
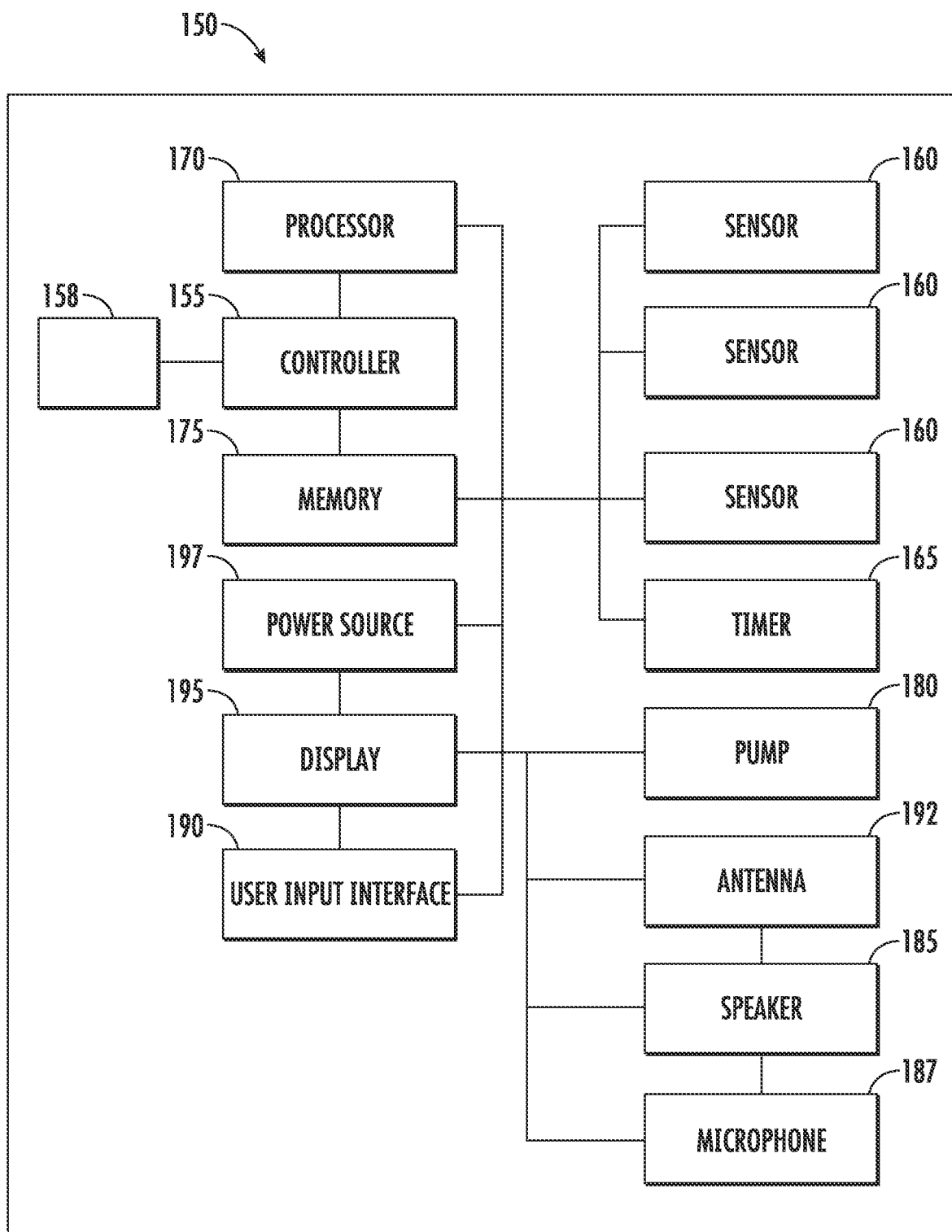
FIG. 2 is a block diagram illustrating an example of an embodiment of a dialysis machine that can be used in the dialysis system of FIG. 1.

Referring to FIG. 2, a schematic of an exemplary embodiment of a dialysis machine such as, for example, dialysis machine 150 is shown. The dialysis machine 150 may be a home dialysis machine, e.g., a PD machine, for performing a dialysis treatment on a patient, and may be included in the system 100 described above with respect to FIG. 1. In use, the dialysis machine 150 may include a controller 155 disposed in the dialysis machine 150. Alternatively, the dialysis machine 150 may be coupled to the controller 155, or other external systems, via a communication port or wireless communication links. The controller 155 may automatically control execution of a treatment function during a course of dialysis treatment.

The controller 155 may be operatively connected to the sensors 160 and deliver a signal to execute a treatment function (e.g., transferring dialysate from the dialysate bag 122 through the heating chamber 152 and then to the patient), or a course of treatment associated with various treatment systems. In some embodiments, a timer 165 may be included for timing the triggering of the sensors 160. The controller 155 may communicate control signals or triggering voltages to the components of the dialysis machine 150, and may include wireless communication interfaces. The controller 155 may detect remote devices to determine if any remote sensors are available to augment any sensor data being used to evaluate the patient. For example, remote devices may include smart phone microphones, video cameras, cameras, thermal imaging cameras, in bed sensors, sleep manager applications and sensors, web cameras, fitness sensors, stand-alone sensors, and the like.

In some embodiments, the machine 150 may also include a processor 170, a memory 175, and/or the controller 155, or combinations thereof and/or the machine 150 may receive signals from the sensor(s) 160 indicating various parameters. Each fluid bag (e.g., the dialysate bags 122) may contain an approximate amount of dialysate, such that "approximate amount" may be defined as a 3L fluid bag containing 3000 to 3150 mL, a 5L fluid bag containing 5000 to 5250 mL, and a 6L fluid bag containing 6000 to 6300 mL. The controller 155 may also detect connection of all fluid bags 122 connected.

Communication between the controller 155 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

In some embodiments, as will be described in greater detail below, the dialysis machine 150 may include at least one pump 180 operatively connected to the controller 155. During a treatment operation, the controller 155 may control the pump 180 for pumping fluid, e.g., fresh and spent dialysate, to and from a patient. The pump 180 may also pump dialysate from the dialysate bag 122 through, for example, the heating chamber 152.

The dialysis machine 150 may also include a user input interface 190, which may include a combination of hardware and software components that allow the controller 155 to communicate with an external entity, such as a patient or other user. These components may be configured to receive information from actions such as physical movement or gestures and verbal intonation. In some embodiments, the components of the user input interface 190 may provide information to external entities. Examples of the components that may be employed within the user input interface 190 include keypads, buttons, microphones, touch screens, gesture recognition devices, display screens, and speakers. The dialysis machine 150 may also include a display 195 and a power source 197.

In some embodiment, the user interface 190 and display 195 may be, for example, a touch screen and a control panel operable by a user (e.g., a caregiver or a patient) to allow, for example, set up, initiation, and/or termination of a dialysis treatment. The touch screen and the control panel may allow an operator to input various treatment parameters to the dialysis machine and to otherwise control the dialysis machine. In addition, the touch screen may serve as the display. The touch screen may function to provide information to the patient and/or the operator of the dialysis system. For example, the touch screen may display information related to a dialysis treatment to be applied to the patient, including information related to a prescription. The touch screen and/or display may include one or more buttons for selecting and/or entering user information.

The dialysis machine 150 may also be connectable for remote communication. For example, the dialysis machine 150 may be configured to connect to a network. The connection to network may be via a wired and/or wireless connection. In one embodiment, the dialysis machine 150 includes, for example, an antenna or other connection component 192 to facilitate connection to a network. The antenna 192 may be, for example, a transceiver for wireless connections and/or other signal processor for processing signals transmitted and received. Other medical devices (e.g., other dialysis machines) or components may be configured to connect to the network and communicate with the dialysis machine 150.

The dialysis machine 150 may also include a speaker 185 and a microphone 187. The controller 155 being operatively connected to the speaker 185 and the microphone 187.

As shown in FIG. 2, the sensors 160 may be included for monitoring parameters and may be operatively connected to at least the controller 155, the processor 170, and/or the memory 175, or combinations thereof. The processor 170 may be configured to execute an operating system, which may provide platform services to application software, e.g., for operating the dialysis machine 150. These platform services may include inter-process and network communication, file system management and standard database manipulation. One or more of many operating systems may be used, and examples are not limited to any particular operating system or operating system characteristic. In some examples, the processor 170 may be configured to execute a real-time operating system (RTOS), such as RTLinux, or a non-real time operating system, such as BSD or GNU/Linux.

In one embodiment, the processor 170 is arranged and configured to communicate with the user interface (e.g., touch screen and control panel). The processor 170 may be configured to receive data from the user interface 190 (e.g., touch screen, control panel), sensors such as, for example, weight, air content, flow, temperature, and/or pressure sensors, and control the dialysis machine 150 based on the received data. For example, the processor 170 may adjust the operating parameters of the dialysis machine 150. According to a variety of examples, the processor 170 may be a commercially available processor such as a processor manufactured by INTEL, AMD, MOTOROLA, and FREESCALE. However, the processor 170 may be any type of processor, multiprocessor or controller, whether commercially available or specially manufactured. For instance, according to one example, the processor 170 may include an MPC823 microprocessor manufactured by MOTOROLA.

The memory 175 may include a computer readable and writeable nonvolatile data storage medium configured to store non-transitory instructions and data. In addition, the memory 175 may include a processor memory that stores data during operation of the processor 170. In some examples, the processor memory includes a relatively high performance, volatile, random access memory such as dynamic random-access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 175 may include executable programs or other code that may be executed by the processor 170. The instructions may be persistently stored as encoded signals, and the instructions may cause the processor 170 to perform the functions described herein. The memory 175 may include information that is recorded, on or in, the medium, and this information may be processed by the processor 170 during execution of instructions. The memory 175 may also include, for example, specification of data records for user timing requirements, timing for treatment and/or operations, historic sensor information, and the like. The medium may, for example, be optical disk, magnetic disk or flash memory, among others, and may be permanently affixed to, or removable from, the controller 155.

The sensor(s) 160 may include a pressure sensor for monitoring fluid pressure of the machine 150, although the sensors 160 may also include any of a heart rate sensor, a respiration sensor, a temperature sensor, a weight sensor, an air sensor, a video sensor, a thermal imaging sensor, an electroencephalogram sensor, a motion sensor, an audio sensor, an accelerometer, a capacitance sensor, or any other suitable sensor. It is appreciated that the sensors 160 may include sensors with varying sampling rates, including wireless sensors.

The controller 155 may be disposed in the machine 150 or may be coupled to the machine 150 via a communication port or wireless communication links, shown schematically as communication element 158. According to various examples, the communication element 158 may support a variety of one or more standards and protocols, examples of which include USB, Wi-Fi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the machine 150, the controller 155 may be operatively connected to any of the sensors 160, the pump 180, and the like. The controller 155 may communicate control signals or triggering voltages to the components of the machine 150. As discussed, exemplary embodiments of the controller 155 may include wireless communication interfaces. The controller 155 may detect remote devices to determine if any remote sensors are available to augment any sensor data being used to evaluate the patient.

Figure 3A:
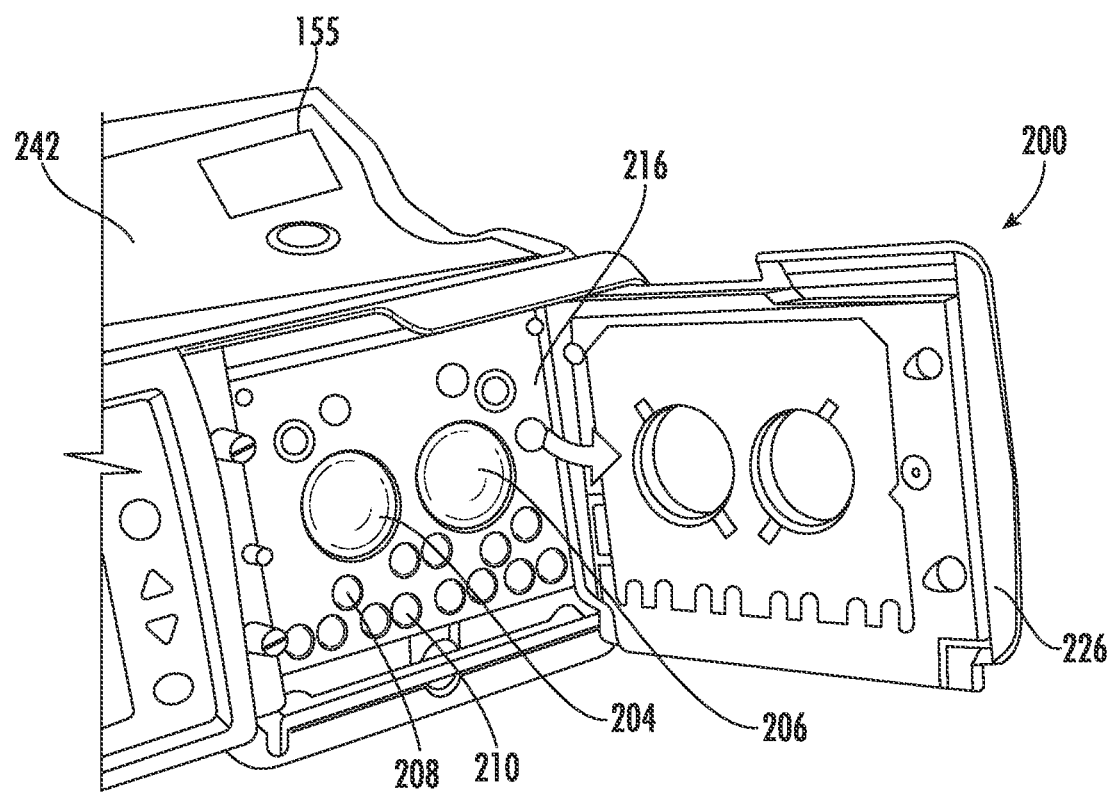
FIGS. 3A-3C illustrate an example of an embodiment of a dialysis machine that can be used in the dialysis system of FIG. 1.
Figure 3B:
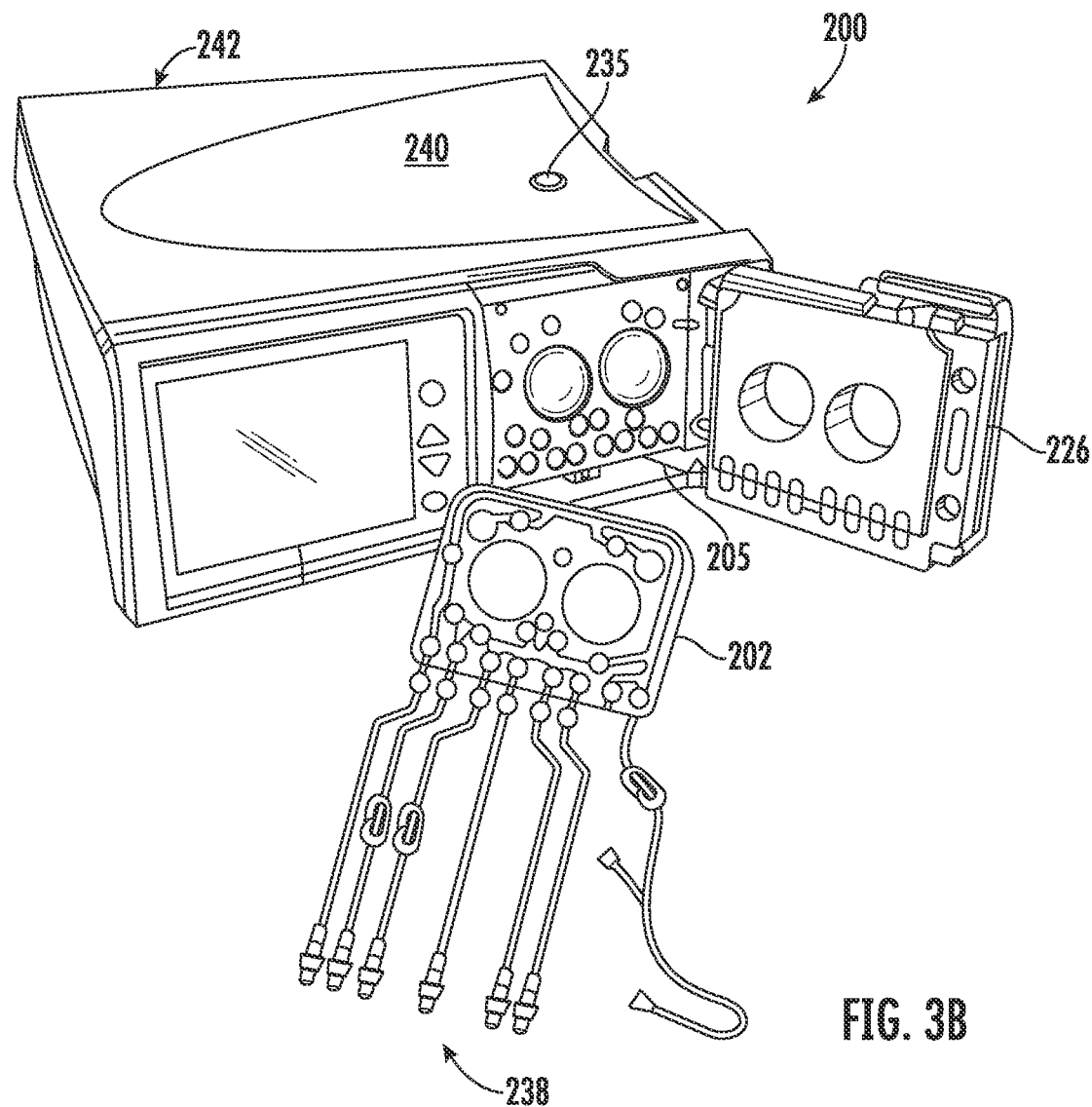
Figure 3C:
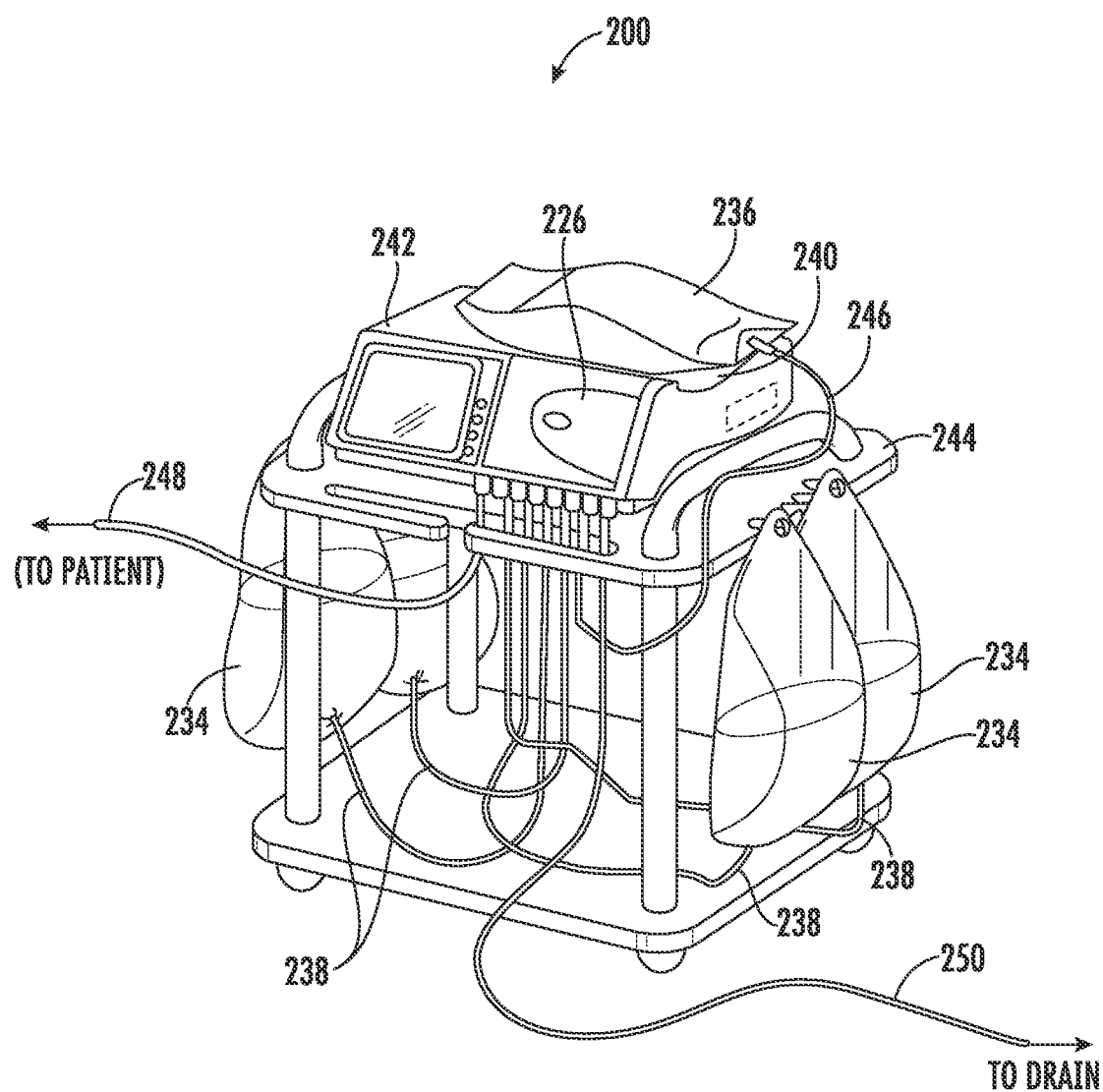

Referring now to FIGS. 3A-3C, an example of an embodiment of a dialysis machine 200 in accordance with the present disclosure is shown. The dialysis machine 200 may include the components described above with respect to the schematic of the system 100 and the machine 150 illustrated in FIGS. 1 and 2. The machine 200 may be configured to provide home dialysis treatment, for example, PD. In some implementations, the dialysis system and machine may be a home PD system, e.g., a PD system configured for use at a patient's home.

The dialysis machine 200 may include a housing 242, a door 226, and a cassette interface including piston or pump heads 204, 206 (used interchangeably herein without the intent to limit) for contacting a cartridge or cassette 202 (used interchangeably without the intent to limit), where the cassette 202 is located within a compartment formed between the cassette interface and the closed door 226 (e.g., cavity 205). Fluid lines (e.g., tubing) may be coupled to the cassette 202 in a known manner, such as via a connector, and may further include valves for controlling fluid flow to and from fluid bags including fresh dialysate and warming pouch. In some embodiments, when a cassette 202 is incorporated, at least a portion of the fluid lines (e.g., tubing) may be integral to the cassette 202. Prior to operation, a user may open the door 226 to insert a fresh cassette 202 and to remove the used cassette 202 after operation.

The cassette 202 may be placed in the cavity 205 of the machine 200 for operation. The machine 200 may manage flowing dialysate into a patient's abdomen, and removal of the used dialysate and waste after a predetermined amount of time. During operation, dialysate fluid may be flowed into a patient's abdomen via the cassette 202, and spent dialysate, waste, and/or excess fluid may be removed from the patient's abdomen via the cassette 202. In some embodiments, a cassette pump plate 216 may be provided, which may contain a pump mechanism and provide openings for the pump heads 204, 206 to operate on an inserted cassette 202.

While the dialysate is present in a peritoneal cavity of the patient, the dialysate may absorb contaminants and/or particulates from the patient's blood. PD uses the patient's peritoneum in the abdomen as a membrane across which fluids and dissolved substances (e.g., electrolytes, urea, glucose, albumin, osmotically active particles, and other small molecules) are exchanged from the blood. PD for a patient may include a total treatment of approximately 10 to 30 liters of fluid, where approximately 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

The machine 200 may operate the pump heads 204, 206 to move the fluid. The pump heads 204, 206 apply force to the cassette 202, that connect a fluid reservoir, e.g., dialysate bags to a catheter at the patient's peritoneum. By operation of the pump heads 204, 206, fresh dialysate may be introduced into the patient's peritoneum. Likewise, the pump heads 204, 206 may draw fluid from the patient's peritoneum into a fluid reservoir or drain to waste. Multiple dialysate bags may be used including a clean fluid reservoir and a waste fluid reservoir. Operation of the pump heads 204, 206 in conjunction with valves such as, for example, valves 208, 210, controls delivery or retrieval of fluid.

In connection with PD machine 200, the heating element 152 may be in the form of a heater tray 240 including a heating element 235 positioned, for example, on top of the housing 242 of the machine 200. The heater tray 240 may be any size and shape to accommodate a bag of dialysate (e.g., a 5L bag of dialysate) for batch heating. In use, for example, dialysate bags 234 may be suspended from hooks on the sides of a cart 244, and a heater bag 236 may be positioned in the heater tray 240. Connectors and tubing ports may connect the dialysate bags 234 and lines for transferring dialysate. Dialysate from the dialysate bags 234 may be transferred to the heater bag 236 in batches. For example, a batch of dialysate may be transferred from one or more dialysate bags 234 to the heater bag 236, where the dialysate is heated by the heating element 235. When the batch of dialysate has reached a predetermined temperature (e.g., approximately 98°–100° F., 37° C.), the batch of dialysate may be flowed into the patient. The dialysate bags 234 and the heater bag 236 may be connected to the cassette 202 via dialysate bag lines or tubing 238 and a heater bag line or tubing 238, respectively. The dialysate bag lines 238 may be used to pass dialysate from dialysate bags 234 to the cassette 202 during use, and a heater bag line 246 may be used to pass dialysate back and forth between the cassette 202 and the heater bag 236 during use. In addition, a patient line 248 and a drain line 250 may be connected to the cassette 202. The patient line 248 may be connected to a patient's abdomen via a catheter and may be used to pass dialysate back and forth between the cassette 202 and the patient's peritoneal cavity by the pump heads 204, 206 during use. The drain line 250 may be connected to a drain or drain receptacle and may be used to pass dialysate from the cassette 202 to the drain or drain receptacle during use.

As previously mentioned, fluid may leak from the cassette 202. Specifically, fluid may leak at the interface between the cassette 202 and the pump mechanism (e.g., pump heads 204, 206) formed in the PD machine 200 (e.g., a leak can develop, for example, at the interface between a piston or pump head of a pump mechanism in the dialysis machine and a membrane proximate a fluid chamber formed in the cassette).

Figure 4:
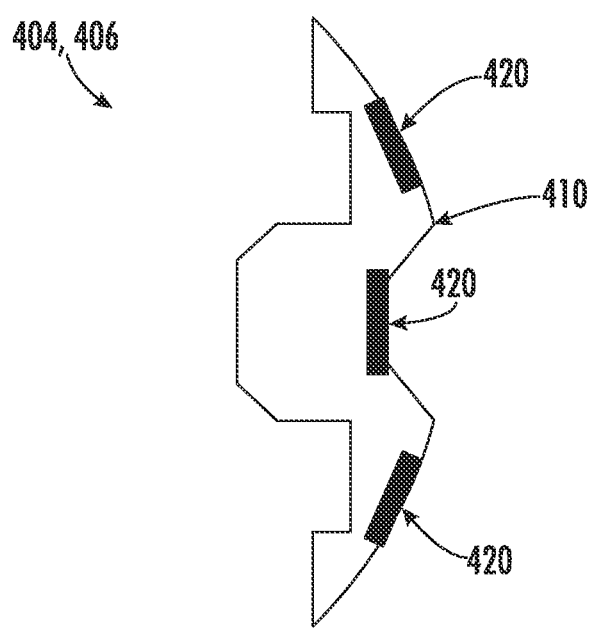
FIG. 4 illustrates a side view of an example of an embodiment of a pump head that may be used in connection with the dialysis machine of FIGS. 2 and 3A-3C in accordance with one or more aspects of the present disclosure.

In accordance with one or more aspects of the present disclosure, the dialysis machine, such as PD machine 150, 200, includes a leak detector or sensor to detect leaks from, for example, the cassette, and to transmit an alarm and/or to shut down the dialysis machine and operation. Referring to FIG. 4, in accordance with one aspect of the present disclosure, the dialysis machine may include a leak detector such as, for example, one or more sensors 420, positioned within or on a surface 410 of a pump head 404, 406 to monitor a leak condition. For example, as shown, the pump head 404, 406 includes a front or contacting surface 410. In use, during transfer of fluid (e.g., dialysate) from the dialysate source to the patient, reciprocating movement of the pump heads 404, 406 against the cassette 202 causes movement of the dialysate. As shown in the illustrated embodiment of FIG. 4, a sensor 420 may be arranged and configured in the front or contacting surface 410 of the pump heads 404, 406 so that, in use, the sensor 420 is arranged and configured to detect a leak or fluid on the outer surface of the cassette 202.

Thus arranged, during normal operation of the dialysis machine 150, 200, fluid (e.g., dialysate) is properly contained within its respective fluid bags and/or fluid lines. The sensor 420 may be configured to monitor the dialysis machine to ensure patient safety. In the event that the sensor contacts, detects, etc. fluid on the outer surface of the cassette 202, the dialysis machine 150, 200 may be configured to react to the leak detection in any number of ways, including initiating alarms and/or causing one or more operational conditions. For example, once a leak has been detected, a signal may be sent from the sensor 420 to, for example, the controller of the dialysis machine to: activate an alarm, halt operations, or a combination thereof. In this manner, the dialysis treatment can be halted and the cassette can be replaced. Thus arranged, a leak can be immediately detected, or within a very short time after the leak occurs, during operation and a signal can be transmitted to the user and/or patient before the dialysis machine incurs severe leak damage.

In use, the sensor 420 may be any suitable sensor now known or hereafter developed, which is arranged and configured to detect fluid on the outer surface of the cassette. For example, in one embodiment, the sensor 420 may be a capacitive sensor. Alternatively, however, other suitable sensors for detecting a leak may be used such as, for example, the sensor 420 may be an electrical circuit, which upon occurrence of a leak causes a short of the electrical circuit, which may in turn trigger a leakage alarm and/or cause other alarm events to occur.

Referring to FIG. 4, in the illustrated embodiment, the sensor 420 is incorporated into the pump head 404, 406 of the dialysis machine 150, 200. For example, the sensor 420 may be a capacitive sensor positioned in the front or contacting surface 410 of the piston or pump head 404, 406 of the pump assembly. Thus arranged, the capacitive sensor 420 is disposed on the contacting surface 410 of the pump head 404, 406 and is moved into contact with the outer surface of the cassette 202. In use, the capacitive sensor 420 is arranged and configured to detect, monitor, measure, etc. fluid on the outer surface of the cassette, on the front or contacting surface 410 of the pump head 404, 406 and/or on the sensor 420.

The sensor 420 can further include one or more wires, cables, etc. for carrying a signal from the sensor 420 to, for example, the controller, processor, etc. of the dialysis machine, which interprets the signal to determine a leak in the cassette. For example, in use, the capacitive sensor 420 can provide a signal that changes when the capacitive sensor 420 detects fluid on the surface 410 of the pump head 404, 406 on the outer surface of the cassette, etc. instead of normal contact with a dry membrane of the cassette. Thus arranged, the dialysis machine can allow for constant monitoring of a leak.

The sensor 420 may have any suitable shape such as, for example, circular, square, etc. and may be positioned anywhere on the surface 410 of the pump head 404, 406 for detecting the presence of fluid on either the surface 410 of the pump head 404, 406 and/or the outer surface of the cassette 202. The sensor 420 may be coupled to the pump head 404, 406 by any suitable mechanism such as, for example, fasteners, adhesive, etc.

Alternatively, and/or in addition, in an another embodiment, a sensor can be positioned on, or adjacent to, an inlet fluid line of the cassette to detect a leak of the fluid (e.g., dialysate) as it enters the cassette and/or dialysis machine.

Once a leak is detected, the dialysis machine 150, 200 may be arranged and configured to take one or more actions. For example, the dialysis machine 150, 200 may be arranged and configured to generate an alarm condition, such as a visual and/or audible notifier. For example, a signal may be sent to the user interface portion of the dialysis machine to indicate the leak, and/or an audio or a light indicator may be triggered. In some embodiments, the dialysis machine 150, 200 may transmit (e.g., via a wireless connection) the alarm condition to a remote location, including but not limited to a doctor's office, hospital, call center, and technical support. For example, the dialysis machine 150, 200 may provide real time remote monitoring of machine operation. The dialysis machine 150, 200 may include a memory for storing data, or may transmit data to a local or remote server at scheduled intervals.

In addition, and/or alternatively, the dialysis machine 150, 200 may be arranged and configured to automatically shut off operation, or allow the user to monitor, pause, and/or cease the dialysis operation based on the leak detection.

Figure 5:
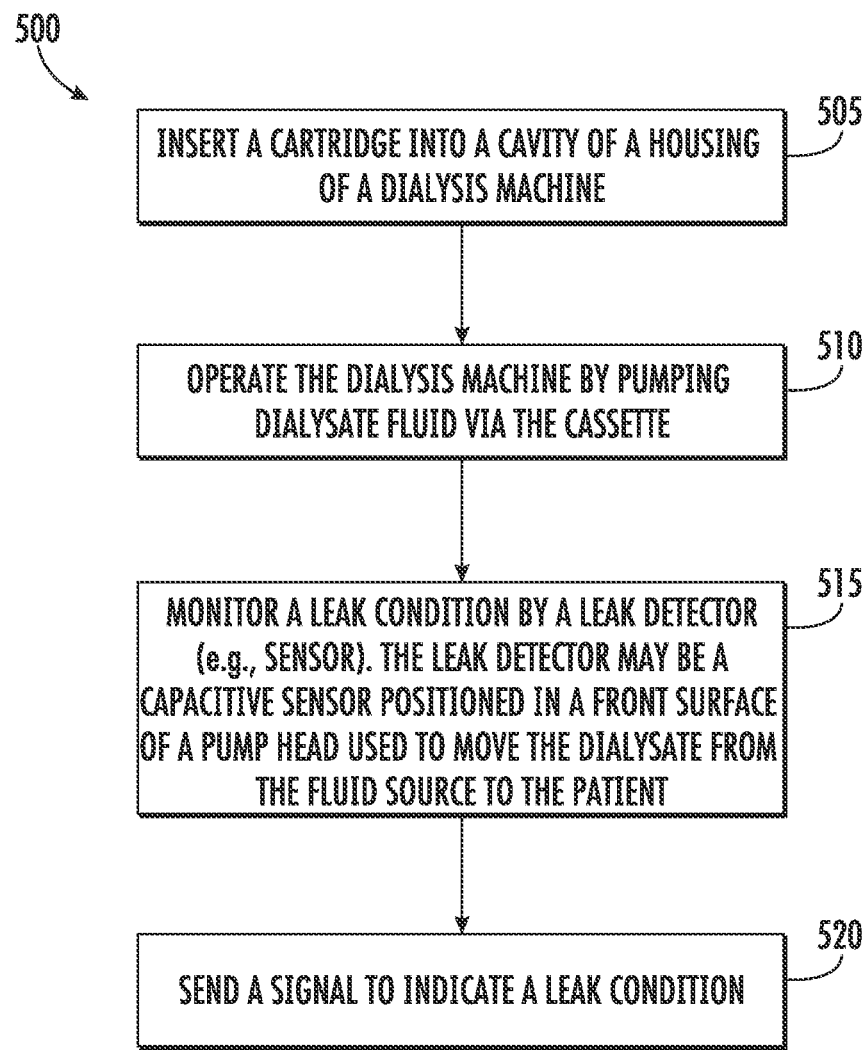
FIG. 5 illustrates a flow diagram of an example of a method of detecting a leak in a dialysis machine according to an embodiment of the present disclosure.

Referring to FIG. 5, a flow diagram 500 of a method of detecting a leak during a dialysis operation according to an embodiment of the present invention is shown. At step 505, components of the dialysis machine 150, 200 are inserted, for example, a cassette 202 may inserted into a cavity of a housing of the dialysis machine. At step 510, the dialysis machine is operated by pumping dialysate fluid via the cassette. As described above, in a peritoneal dialysis operation, fresh dialysate may be pumped into an abdomen of a patient, and spent dialysate, including waste and excess fluid, may flow out of the patient's abdomen. At step 515, a leak condition of the dialysis machine is monitored by the leak detector (e.g., sensor). The leak detector may be a capacitive sensor positioned in a front surface of a pump head used to move the dialysate from the fluid source to the patient. At step 520, when a leak is detected in the dialysis machine, a signal is transmitted from the sensor to the processor of the machine. As described above, the machine may send an audible or a visual indication of the leak condition, and alternatively, or additionally, automatically stop dialysis operation.

The system described herein has been explained in connection dialysis machines having a particular configuration. It is contemplated that the system described herein may be used with dialysis machines having other configurations, for example, different types of dialysis machines and/or dialysis machines having cassettes positionable in other configurations and having other features. The system described herein may be used with any appropriate dialysis machine and/or other medical devices utilizing disposable cassettes that would benefit from leak detection.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

While the systems and techniques described herein for detecting leaks have been largely explained with reference to a dialysis machine, in particular, a peritoneal dialysis machine, the systems and techniques described for detecting leaks may be used in connection with other types of medical treatment systems and/or machines, such as a hemodialysis machine or other medical treatment device involving medical fluids. In some implementations, the dialysis machine may be configured for use in a patient's home (e.g., a home dialysis machine). The home dialysis machine can take the form of a peritoneal dialysis machine or a home hemodialysis machine.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A dialysis system for conducting a dialysis treatment, comprising:
    a dialysis machine for transferring dialysate to a patient from a dialysate source, the dialysis machine including a housing including a cavity, a pump positioned within the housing, and a sensor associated with the pump; and
    a cassette positionable within the cavity, the cassette being in fluid communication with the patient and the dialysate source;
    wherein, when the cassette is positioned within the cavity, movement of the pump causes a front contacting surface of the pump to contact the cassette to cause dialysate to be transferred from the dialysate source to the patient, the sensor being positioned on the front contacting surface of the pump to detect a presence of fluid on one of an outer surface of the cassette or the front contacting surface of the pump.

2. The dialysis system of claim 1, wherein the sensor is a capacitive sensor arranged and configured to detect the presence of fluid.

3. The dialysis system of claim 2, wherein the capacitive sensor is positioned within the pump.

4. The dialysis system of claim 1, wherein the sensor is configured to send a signal based on a detection of fluid with the sensor to indicate a leak condition; wherein the signal is sent to a user interface of the dialysis machine, an audible indicator, or a light indicator, or a combination thereof.

5. The dialysis system of claim 4, wherein the dialysis machine is arranged and configured to automatically terminate the transfer of dialysate to the patient from the dialysate source upon receipt of the signal.

6. A dialysis system for conducting a dialysis treatment, comprising:
    a dialysis machine arranged and configured to transfer dialysate to a patient from a dialysate source, the dialysis machine including a housing including a cavity, and a pump positioned within the housing for facilitating transfer of the dialysate; and
    a capacitive sensor positioned within the pump, the pump including a front contacting surface configured to contact a cassette positioned with cavity of the housing, the cassette being in fluid communication with the patient and the dialysate source, the capacitive sensor disposed within the front contacting surface of the pump, or on the front contacting surface of the pump, or a combination thereof, wherein a leak is detectable in response to fluid contacting the capacitive sensor.

7. The dialysis system of claim 6, wherein during operating the dialysis machine, the pump contacts the cassette, the capacitive sensor being arranged and configured to detect a presence of fluid.

8. The dialysis system of claim 7, wherein the capacitive sensor is arranged and configured to detect the presence of fluid on one of an outer surface of the cassette and on the front contacting surface of the pump.

9. The dialysis system of claim 6, wherein in response to the leak, the dialysis machine is arranged and configured to transmit a signal to indicate a leak condition, the signal is sent to a user interface of the dialysis machine, an audible indicator, or a light indicator, or a combination thereof.

* * * * *